United States Patent
Mathaneswaran et al.

(10) Patent No.: US 11,521,519 B2
(45) Date of Patent: Dec. 6, 2022

(54) CRANIAL BIO-MODEL COMPRISING A SKULL LAYER AND DURA LAYER AND METHOD OF MANUFACTURING A CRANIAL BIO-MODEL

(71) Applicant: UNIVERSITI MALAYA, Kuala Lumpur (MY)

(72) Inventors: Vickneswaran A/L Mathaneswaran, Kuala Lumpur (MY); Zainal Ariff Bin Abdul Rahman, Kuala Lumpur (MY); Yuwaraj Kumar A/L Balakrishnan, Kuala Lumpur (MY); Su Tung Tan, Kuala Lumpur (MY)

(73) Assignee: Universiti Malaya, Kuala Lumpur (MY)

( * ) Notice: Subject to any disclaimer, the term of this patent is extended or adjusted under 35 U.S.C. 154(b) by 504 days.

(21) Appl. No.: 16/317,541

(22) PCT Filed: Jul. 12, 2017

(86) PCT No.: PCT/MY2017/050038
§ 371 (c)(1),
(2) Date: Jan. 12, 2019

(87) PCT Pub. No.: WO2018/012961
PCT Pub. Date: Jan. 18, 2018

(65) Prior Publication Data
US 2019/0236984 A1    Aug. 1, 2019

(30) Foreign Application Priority Data
Jul. 12, 2016  (MY) .............................. PI2016001296

(51) Int. Cl.
*G09B 23/30* (2006.01)
*A61B 34/10* (2016.01)

(52) U.S. Cl.
CPC .............. *G09B 23/30* (2013.01); *A61B 34/10* (2016.02)

(58) Field of Classification Search
CPC ................................ G09B 23/28; G09B 23/30
(Continued)

(56) References Cited

U.S. PATENT DOCUMENTS 8,105,089 B2 *  1/2012  Hudson ................. G09B 23/34
                                                    434/274
8,915,743 B2 * 12/2014  Meglan ................ G09B 23/283
                                                    434/262
(Continued)

OTHER PUBLICATIONS

International Search Report and Written Opinion of International Search Authority for International Application No. PCT/MY2017/050038.
(Continued)

*Primary Examiner* — Kurt Fernstrom
(74) *Attorney, Agent, or Firm* — Preston Smirman; Smirman IP Law, PLLC

(57) ABSTRACT

A cranial bio-model including a skull layer and a dura layer and method of manufacturing a cranial bio-model. A three dimensional bio-model for simulating a simulated cranial surgical procedure, the bio-model comprises a synthetic skull layer, a synthetic dura layer under the synthetic skull layer, and a spacer layer between the synthetic skull layer and the synthetic dura layer. The bio-model may be manufactured based on medical image data using three-dimensional printing.

10 Claims, 4 Drawing Sheets

(58) Field of Classification Search
USPC .................................... 434/262, 267, 274
See application file for complete search history.

(56) References Cited

U.S. PATENT DOCUMENTS

| | | | | |
|---|---|---|---|---|
| 10,181,270 | B1* | 1/2019 | Fuller | G09B 23/30 |
| 10,359,348 | B1* | 7/2019 | Lytle | G09B 9/00 |
| 2007/0148633 | A1 | 6/2007 | Sakezles | |
| 2009/0149977 | A1* | 6/2009 | Schendel | G16H 50/50 700/98 |
| 2010/0167254 | A1* | 7/2010 | Nguyen | G09B 23/30 434/272 |
| 2014/0024004 | A1 | 1/2014 | Tvermoes et al. | |
| 2014/0302306 | A1 | 10/2014 | Merkle et al. | |
| 2014/0370475 | A1* | 12/2014 | Bova | G09B 23/00 434/267 |
| 2015/0352250 | A1* | 12/2015 | Dalman | G09B 23/30 523/115 |
| 2016/0027341 | A1* | 1/2016 | Kerins | B29C 39/38 434/270 |
| 2016/0155364 | A1 | 6/2016 | Piron et al. | |
| 2016/0287339 | A1* | 10/2016 | Bin Abdul Rahman | A61B 8/00 |
| 2017/0360578 | A1* | 12/2017 | Shin | B33Y 50/00 |
| 2019/0021865 | A1* | 1/2019 | Vogtmeier | A61B 6/5205 |
| 2019/0090824 | A1* | 3/2019 | Brunicardi | A61B 8/523 |

OTHER PUBLICATIONS

International Preliminary Report on Patentability dated Jan. 15, 2019.
Waran, V. et al., "Utility of Multimaterial 3D Printers in Creating Models With Pathological Entities to Enhance the Training Experience of Neurosurgeons," Journal of Neurosurgery, Feb. 2014, vol. 120, No. 2, pp. 489-492.
Waran, V. et al., "Injecting Realism in Surgical Training—Initial Simulation Experience With Custom 3D Models," Journal of Surgical Education, Jan. 2013, pp. 1-5.
Waran, V. et al., "Three-Dimensional Anatomical Accuracy of Cranial Models Created by Rapid Prototyping Techniques Validated Using a Neuronavigation Station," Journal of Clinical Neuroscience, 2012, vol. 19, pp. 574-577.
Jardini, A.L. et al., "Cranial Reconstruction: 3D Biomodel and Custom Built Implant Created Using Additive Manufacturing," Journal of Cranio-Maxillo-Facial Surgery, 2014, vol. 42, pp. 1877-1884.
Oishi, M. et al., "Interactive Presurgical Simulation Applying Advanced 3D Imaging and Modeling Techniques for Skull Base and Deep Tumors," Journal of Neurosurgery, Jul. 2013, vol. 119, No. 1, pp. 94-105.

* cited by examiner

CRANIAL BIO-MODEL COMPRISING A SKULL LAYER AND DURA LAYER AND METHOD OF MANUFACTURING A CRANIAL BIO-MODEL

FIELD OF THE INVENTION

Embodiments of the present invention relate to three dimensional bio-models of cranial regions for use in simulating or practicing surgical procedures; and the manufacture of such bio-models.

BACKGROUND OF THE INVENTION

Surgery is a difficult discipline to master. In order to develop and perfect their surgical skills, trainees and junior surgeons must repeatedly practice surgical procedures. Traditionally trainee surgeons have used cadavers to develop and practice their technique. The use of cadavers presents a number of issues: in many countries the use of cadavers is restricted for ethical and religious reasons; and the cost associated with preservation and disposal of is high. Further, in order to simulate many medical procedures an accurate representation of a specific pathology is required. An example of this is the simulation of the procedure required for the removal of a tumor. In such a case, the position, orientation, size and nature of the tumor will be unique to the pathology of a specific patient. Therefore a simulation based on a normal anatomy without the tumor will be of little or no benefit in for a surgeon preparing for the removal of a tumor.

Recent developments in three-dimensional printing techniques allow the production of three-dimensional bio-models of parts of the human anatomy which can assist surgeons in practicing their technique. The production of bio-models by these techniques allows accurate representations of the human body to be produced. The bio-models may be based on a specific patient and include accurate representations of the anatomy specific to that patient. Surgeons may use such bio-models to simulate and plan surgeries for specific patients as well as to practice general surgical techniques. In addition to accurately reproducing the anatomy of a patient, such bio-models must also accurately reproduce the response of a real anatomy to surgical tools.

SUMMARY OF THE INVENTION

According to a first aspect of the present invention there is provided a three dimensional bio-model for simulating a simulated cranial surgical procedure. The bio-model comprises a synthetic skull layer, a synthetic dura layer under the synthetic skull layer, and a spacer layer between the synthetic skull layer and the synthetic dura layer.

The inclusion of a spacer layer between the synthetic skull layer and the synthetic dura provides a gap between the two layers. In the true cranial anatomy, the dura layer is in contact with the skull but not adherent to it. Surgical tools such as drills for drilling a burr hole in the skull are often provided with a clutch that releases when there is a drop in resistance due to the drill having passed through the skull of a patient. Embodiments of the present invention aim to simulate this in a bio-model. The spacer layer provides a gap between the synthetic skull layer and the synthetic dura layer which allows the clutch of a drill to release so that a simulated surgical procedure on the bio-model mimics the actual surgery.

In an embodiment, the bio-model further comprises a synthetic skin layer over the synthetic skull layer. The bio-model may also further comprise a synthetic anatomical structure under the synthetic dura layer. This synthetic anatomical structure may simulate a tumor to be removed in the simulated surgical procedure.

The dura layer may have a thickness in the range 1 mm to 2 mm.

In an embodiment the three dimensional bio-model is configured to be insertable into a slot in a base piece.

In an embodiment the three dimensional bio-model comprises a base piece and an insert, the base piece defining a slot, the insert being configured to fit into the slot, the insert comprising the synthetic skull layer, the synthetic dura layer under the synthetic skull layer, and the spacer layer.

The insert provides an accurate representation of the internal anatomy which may be cut or otherwise changed during a simulated procedure. Therefore, the insert can only be used for one simulated procedure. Since the base part is not altered during a simulated procedure it can be reused. Therefore only the insert is discarded following a simulated procedure. This reduces the cost of each individual simulation since only the insert must be replaced.

The surface of the base part may accurately represent the surface of a part of a body such as a head. This allows surgical navigation systems to be used during the simulated surgical procedure. Surgical navigation systems such as the Medtronic StealthStation S7 System use optical navigation cameras to assist a surgeon during surgery. The provision of a base part which accurately reproduces the surface features in an area around the simulated procedure location allows the use of the navigation system to be incorporated in the simulation of the surgical procedure.

Alternatively, the three dimensional bio-model may be produced as a single part.

According to a second aspect of the present invention, there is provided a method of manufacturing a three dimensional bio-model. The method comprises receiving medical image data for a cranial region. The medical image data may be captured from medical imaging apparatus such as a magnetic resonance imaging (MRI) apparatus, a computed tomography (CT) apparatus, an x-ray imaging apparatus, or an ultrasound apparatus. Three dimensional structure data for the cranial region from the medical image data is generated from the medical image data. The three dimensional structure data indicates a skull layer and a dura layer. Three dimensional bio-model structure data is then generated from the three dimensional structure data by adding by adding an indication of a spacer layer between the skull layer and the dura layer. The bio-model structure data is then three dimensional printed to provide a three dimensional bio-model structure.

The use of three dimensional printing technology allows a bio-model to be produced that accurately represents the anatomy of a patient and the pathology of any diseases from which the patient is suffering.

The method may further comprise receiving a user input identifying the dura layer. Alternatively, the medical image data may be segmented medical image data comprising indications of the skull layer and the dura layer. The medical image data may be segmented. The segmentation may provide labels indicating parts of the anatomical structure. This segmentation may be applied by a clinician or may be automatically applied using image recognition software.

The bio-model may be printed as a plurality of separate parts which are assembled to form the complete bio-model.

BRIEF DESCRIPTION OF THE DRAWINGS

In the following, embodiments of the present invention will be described as non-limiting examples with reference to the accompanying drawings in which.

DETAILED DESCRIPTION

Figure 1:
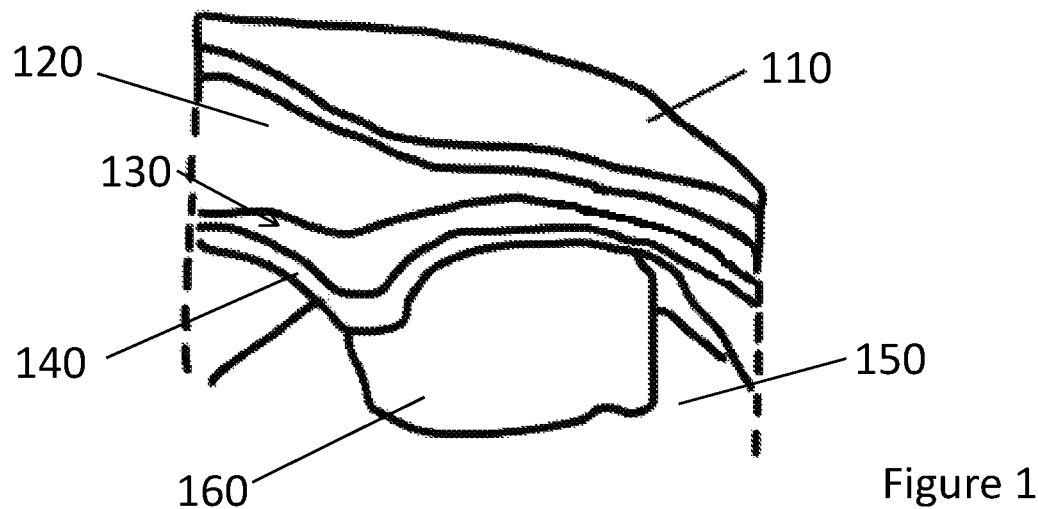
FIG. 1 shows a cranial bio-model 100 according to an embodiment of the present invention.

FIG. 1 shows a cranial bio-model 100 according to an embodiment of the present invention. The cranial bio-model 100 mimics the anatomy of part of a human head. The cranial bio-model 100 comprises a synthetic skin layer 110. Under the synthetic skin layer 110 there is a synthetic skull layer 120. There is a synthetic dura layer 140 below the synthetic skull layer 120. The synthetic dura layer 140 covers a synthetic brain tissue 150. A synthetic tumor 160 is located in the synthetic brain tissue 150. The cranial bio-model 100 further comprises a spacer layer 130 arranged between the synthetic dura layer 140 and the synthetic skull layer 120.

The cranial bio-model 100 is used to simulate a surgical procedure. An example of the simulated surgical procedure is the removal of a brain tumor by craniotomy. A craniotomy involves temporarily removing a bone flap from the skull to access the brain. The procedure for removing the bone flap involves drilling a series of small holes, called burr holes or pilot holes, in the skull. Usually, these holes are drilled at an angle perpendicular to the surface of the cranium. The holes are positioned around the periphery of the proposed bone flap. The tool for drilling the burr holes is generally equipped with a clutch which automatically disengages once it touches softer tissue, thus preventing tears in the dura. This clutch disengages when there is a drop in resistance. A craniotome is then used to cut the bone between each adjacent hole. The craniotome typically comprises a saw with a guard plate at the foot to separate the bone from the dura beneath it.

In the anatomy of a human cranial region, the dura is located beneath the skull. The dura is in contact with the skull but not adherent to the skull. The surgical tools discussed above are designed to function with this anatomy. Embodiments of the present invention allow the function of the surgical tools discussed above to take place when a cranial bio-model is used to simulate a surgical procedure such as a craniotomy.

Figure 2:
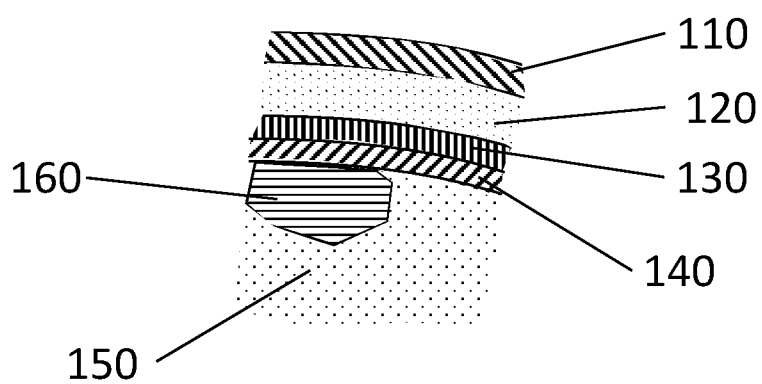
FIG. 2 shows a cross section through a cranial bio-model according to an embodiment of the present invention.

FIG. 2 shows a cross section through a cranial bio-model according to an embodiment of the present invention. As shown in FIG. 2 the cranial bio-model 100 comprises a synthetic skin layer 110 with a synthetic skull layer 120 beneath the synthetic skin layer 110. A spacer layer 130 is located beneath the synthetic skull layer 120. The spacer layer 130 separates the synthetic skull layer 120 from a synthetic dura layer 140. The synthetic dura layer 140 covers synthetic brain tissue 150. A synthetic tumor 160 is located in the synthetic brain tissue 150.

During a simulated surgical procedure, the spacer layer 130 separates the synthetic skull layer 120 from the synthetic dura layer 140. This separation of the synthetic skull later 120 from the synthetic dura layer 140 means that when a hole is drilled through the synthetic skull layer 120, there is a gap to the synthetic dura layer 140. This gap which results from the spacer layer 130 means that there is a drop in resistance so that the clutch on the drill disengages. Thus the use of the drill is accurately simulated. Additionally, the spacer layer 130 allows the use of a craniotome to be accurately simulated.

The dura layer may be formed from a rubber like material such as TangoPlus produced by Stratasys.

In an embodiment, the cranial bio-model is an insert which fits into a slot in a base piece. This is shown in FIG. 3.

Figure 3:
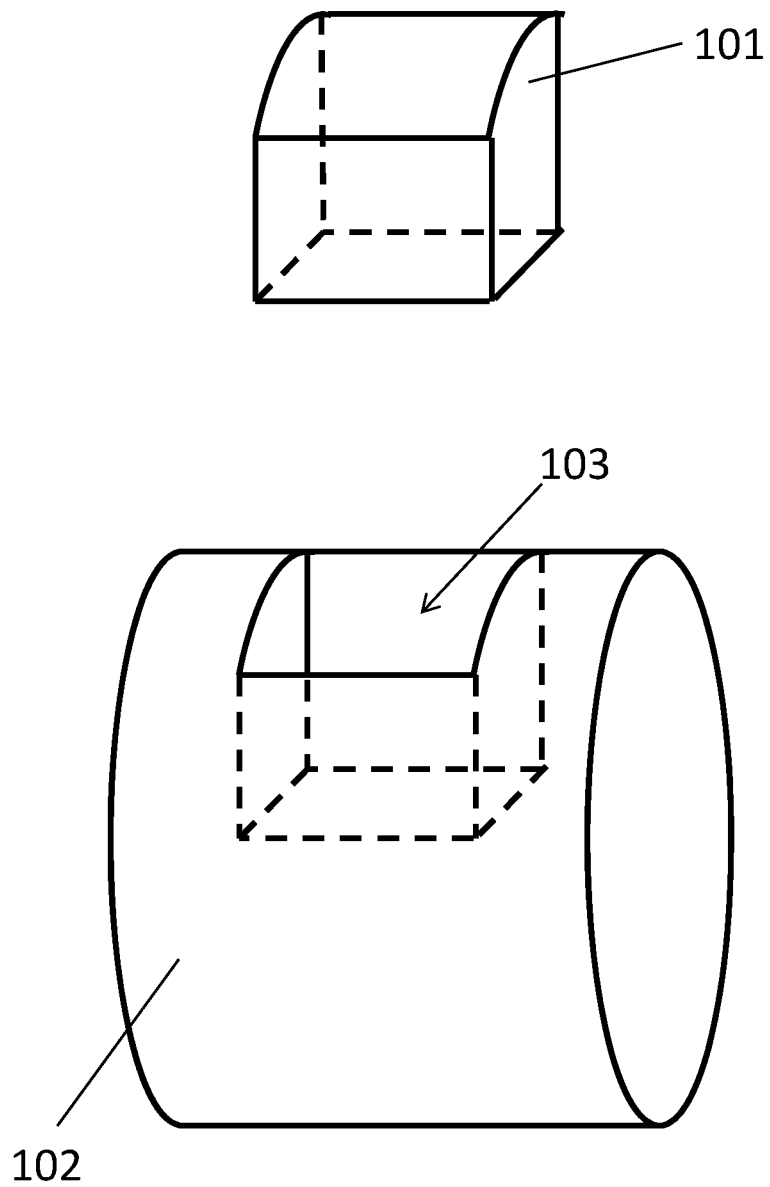
FIG. 3 shows a bio-model which comprises an insert according to an embodiment of the present invention.

FIG. 3 shows a cranial bio-model according to an embodiment of the present invention which comprises a base piece and an insert. The insert 101 is as described above in relation to FIGS. 1 and 2. The sides of the insert may be formed as walls. The base piece 102 has a slot 103 into which the insert 101 can be fitted.

The exterior surface of the base piece 102 has contours and features which correspond to the exterior of part of the head. For example, the base piece may include the contours and features of a human head or the facial features of a human head.

While the exterior of the base piece 102 is shaped to simulate the corresponding parts of the human anatomy, the interior structure is not. The interior of the base piece 102 may be solid or hollow. During a simulated surgical procedure the insert 101 provides a simulation of the interior structure of the body being operated on. The base piece 102 provides a simulation of the exterior of the patient.

During many surgical procedures, surgical navigation systems are used by the surgeon for guidance. An example of a surgical navigation system is the Medtronic StealthStation S7 System. Such navigation systems use optical navigation to determine locations on a patient's body. The base piece 102 and insert 101 may be produced using scan data from a patient as described below with reference to FIG. 6 in more detail. Since the exterior surface of the base piece 102 will correspond to this scan data, the base piece 102 provides an accurate simulation of the surgical procedure using the navigation system.

The insert 101 includes a top layer of synthetic skin to simulate the skin of the patient during the simulated surgical procedure. During simulation of the surgical procedure, the surgeon will cut an incision or insert a probe through this skin layer. In addition, the surgeon may cut or alter the internal structure of the insert 101. Therefore, the insert 101 can normally only be used for one simulated surgical procedure and is then discarded. Since no changes are made to the base piece 102, it can be reused when the simulation is repeated, for example if the surgeon wishes to practice the same procedure a number of times or to alter certain aspects during planning of a surgical procedure. Therefore the amount of the model which is discarded can be reduced by providing a base piece which can be reused.

Figure 4:
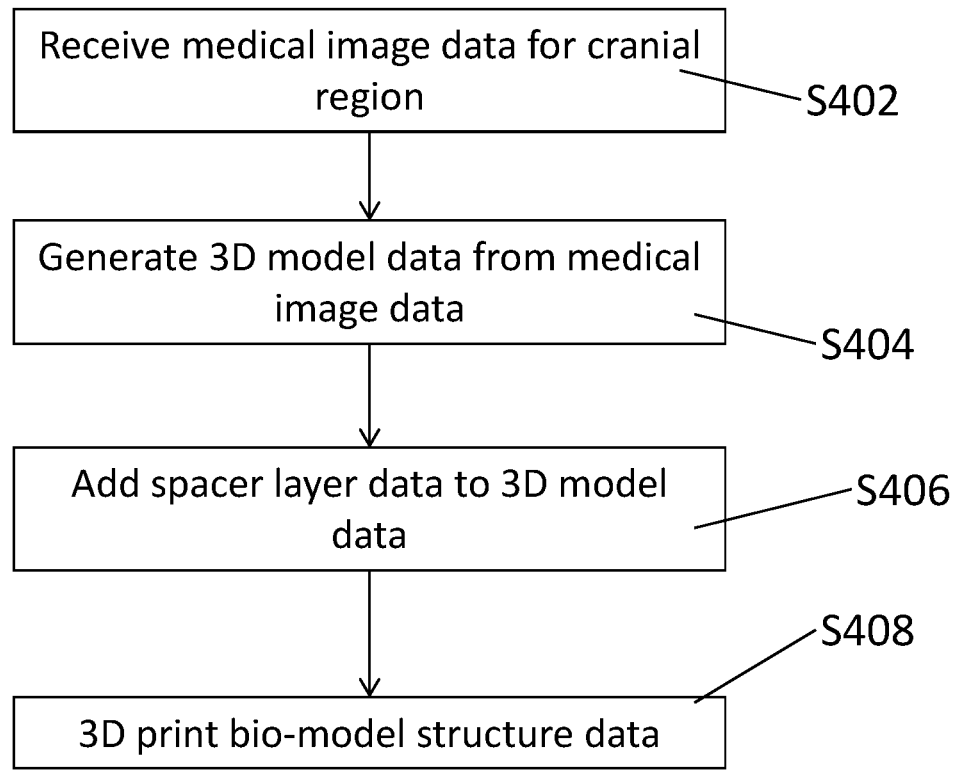
FIG. 4 is a flow chart showing a method of manufacturing a cranial bio-model according to an embodiment of the present invention.
Figure 5:
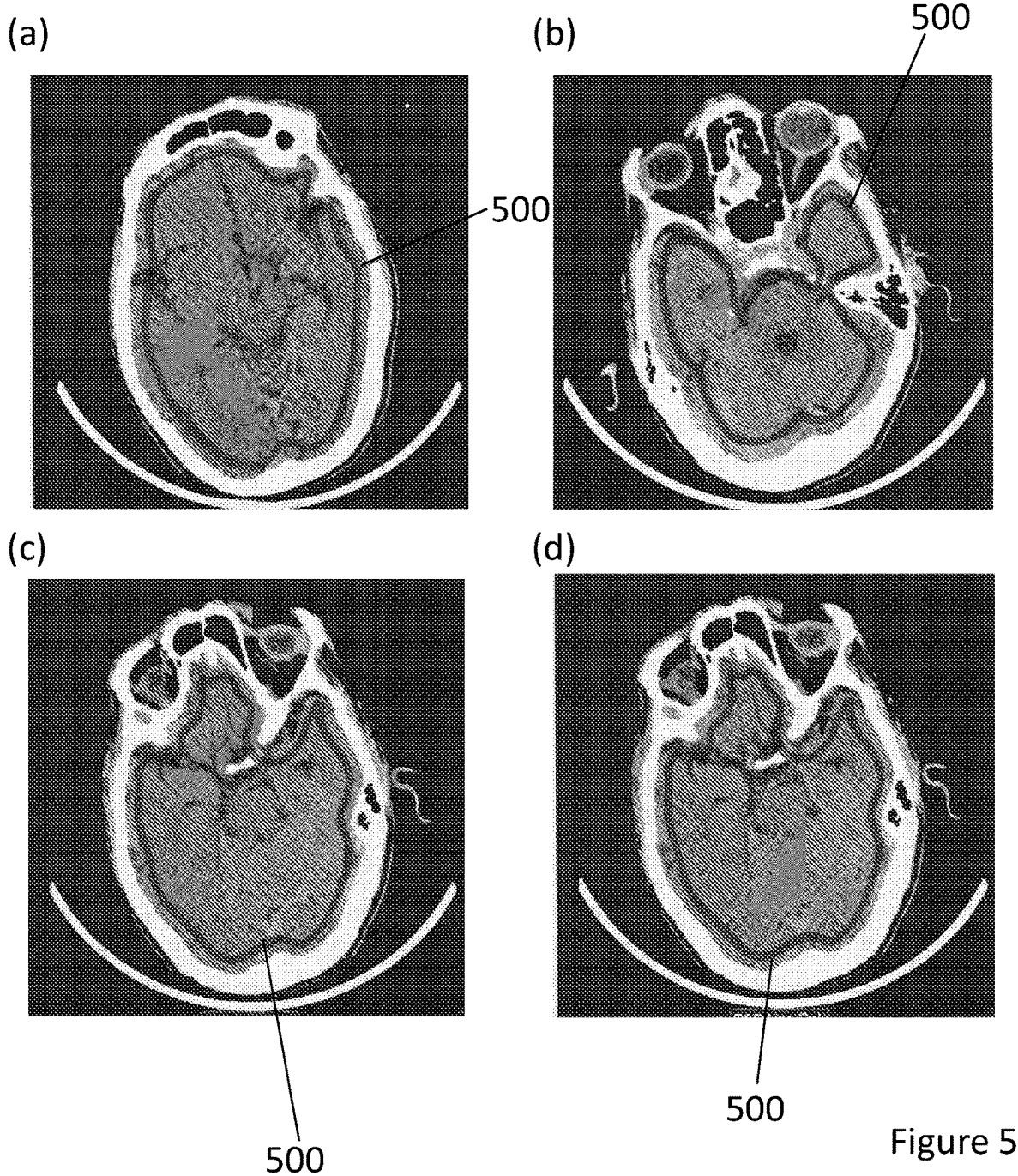
FIGS. 5a to 5d show the identification of dura on medical image data in an embodiment of the present invention.

FIG. 4 is a flow chart showing a method of manufacturing a cranial bio-model according to an embodiment of the present invention. The method shown in FIG. 4 may be carried out using a computer and a three dimensional printer.

In step S402, medical image data for a cranial region is received the computer. The medical image data may be stored data obtained from a medical imaging apparatus such as a magnetic resonance imaging (MRI) apparatus, a computed tomography (CT) apparatus, an X-ray imaging apparatus, or an ultrasound imaging apparatus. The medical image data may be in the Digital Imaging and Communications (DICOM) format.

The medical image data received in step S402 may be segmented, that is, the various layers and tissues in the images may be labelled. This labelling may be implemented automatically using image analysis, or the images may be segmented manually by an operator.

In step S404, three dimensional model data is generated from the medical image data. The three dimensional model data is generated using a 3D conversion algorithm which generates three dimensional surfaces from the medical image data. Algorithms such as the marching cube algorithm, Delaunay's triangulation algorithm or a combination of the two may be used. The result of step S404 is a three dimensional model of the cranial region.

In step S406, spacer layer data is added to the three dimensional model of the anatomical structure. The spacer layer data indicates the location and thickness of a spacer layer in the cranial bio-model. As discussed above, the spacer later is located between the skull and the dura layer. The spacer layer data may be added using computer aided design (CAD) software.

In step S408, the cranial bio-model 100 is printed using three dimensional printing. The shape of the structures and materials to be used for each anatomical region can be predetermined in the 3D data. By this way of predetermination and modification, accurate shape and material can be assigned to each anatomical region, beneficial specifically for pre-surgical training, surgical simulation and surgical training.

The method described above may comprise receiving a user input identifying the dura layer. The identification of the dura layer is described in more detail below with reference to FIGS. 5a to 5d.

FIGS. 5a to 5d show the identification of dura on medical image data in an embodiment of the present invention. Each of FIGS. 5a to 5d show cross sections through a cranial region of a patient obtained from Computed Tomography (CT) scan. In an embodiment of the present invention, the dura layer is labelled by a clinician. As shown in each of FIGS. 5a to 5d, the dura region 500 is identified by a user.

In one embodiment, the bio-model is 3D printed together as a single structure using additive manufacturing technology. Alternatively, the bio-model 100 may be printed as a number of separate parts which are assembled.

In an embodiment, the 3D data is subjected to a rapid additive manufacturing technique where layers of material are added upon one another to form the 3D anatomical structure. The rapid additive manufacturing techniques used to produce the bio-model 100 may include layered manufacturing, direct digital manufacturing, laser processing, electron beam melting, aerosol jetting, inkjet printing or semi-solid free-form fabrication. The 3D data enables the rapid additive manufacturing machine to sequentially build up many thin layers upon another to build the 3D bio-model.

As described above, embodiments of the present invention provide a bio-model which accurately simulates the response of the skull and dura to surgical procedures. The bio-model is produced using medical image data and there provides a 3D model that accurately simulates the actual anatomical structure. The 3D model represents the selected structures, organs or any region of interest and pathology of the disease.

Embodiments of the present invention provide an accurate anatomical model which serves as tool for a better understanding on the condition of a patient or the procedure for operating on a patient.

As described above, embodiments of the present invention provide a method of mimicking the human soft tissue or alternatively mentioned as dura or dura layer, which accurately simulates the actual human tissue which is present the skull structure of human.

Whilst the foregoing description has described exemplary embodiments, it will be understood by those skilled in the art that many variations of the embodiment can be made within the scope and spirit of the present invention.

The invention claimed is:

1. A three dimensional bio-model for simulating a simulated cranial surgical procedure, comprising:
   a synthetic skull layer;
   a synthetic dura layer under the synthetic skull layer; and
   a spacer layer between the synthetic skull layer and the synthetic dura layer to simulate a gap therebetween such that the spacer layer results in a drop in resistance to disengage a clutch as it penetrates the spacer layer during the simulated cranial surgical procedure.

2. The three dimensional bio-model according to claim 1, further comprising a synthetic skin layer over the synthetic skull layer.

3. The three dimensional bio-model according to claim 1, further comprising a synthetic anatomical structure under the synthetic dura layer.

4. The three dimensional bio-model according to claim 1, wherein the synthetic dura layer has a thickness in the range 1 mm to 2 mm.

5. The three dimensional bio-model according to claim 1 configured to be insertable into a slot in a base piece.

6. The three dimensional bio-model according to claim 1, further comprising a base piece and an insert, the base piece defining a slot, the insert being configured to fit into the slot, the insert comprising the synthetic skull layer, the synthetic dura layer under the synthetic skull layer, and the spacer layer.

7. The three dimensional bio-model according to claim 6, the surface of the base piece having contours and/or features selected to mimic an external anatomy.

8. A method of manufacturing a three dimensional bio-model, comprising:
   receiving medical image data for a cranial region;
   generating three dimensional model data for the cranial region from the medical image data, the three dimensional model data indicating a skull layer and a dura layer;
   generating bio-model structure data from the three dimensional structure data, by adding an indication of a spacer layer between the skull layer and the dura layer to simulate a gap therebetween such that the spacer layer results in a drop in resistance to disengage a clutch as it penetrates the spacer layer during the simulated cranial surgical procedure; and
   three dimensional printing the bio-model structure data to provide a three dimensional bio-model structure.

9. The method according to claim 8, wherein further comprising receiving a user input identifying the dura layer.

10. The method according to claim 8, wherein the medical image data is segmented medical image data comprising indications of the skull layer and the dura layer.

* * * * *